United States Patent [19]

Reuter

[11] 3,980,524
[45] Sept. 14, 1976

[54] AIR TESTING DEVICE

[75] Inventor: Adolf Karl Reuter, Marburg, Germany

[73] Assignee: Filba Adolf Reuter Kommanditgesellschaft Marburg an der Lahn, Marburg, Germany

[22] Filed: Jan. 4, 1974

[21] Appl. No.: 431,143

[30] Foreign Application Priority Data
Jan. 12, 1973   Germany.............................. 2301385

[52] U.S. Cl. ............................................... 195/139
[51] Int. Cl.² ............................................... C12B 1/00
[58] Field of Search................. 195/103.5, 127, 139, 195/142, 143; 23/253 TP, 254 R

[56] References Cited
UNITED STATES PATENTS 3,127,329   3/1964   Andersen....................... 195/142 X
3,232,094   2/1966   Teschner....................... 195/103.5 X
3,551,295   12/1970  Dyer.............................. 195/103.5
3,576,721   4/1971   Mason........................... 195/139

Primary Examiner—A. Louis Monacell
Assistant Examiner—R. B. Penland
Attorney, Agent, or Firm—Neuman, Williams, Anderson & Olson

[57] ABSTRACT

A portable instrument for testing air or other gaseous bodies for foreign substances such as germs and bacteria employs a cultural substrate against which a surrounding portion of the atmosphere is urged by rotating impeller blades.

11 Claims, 13 Drawing Figures

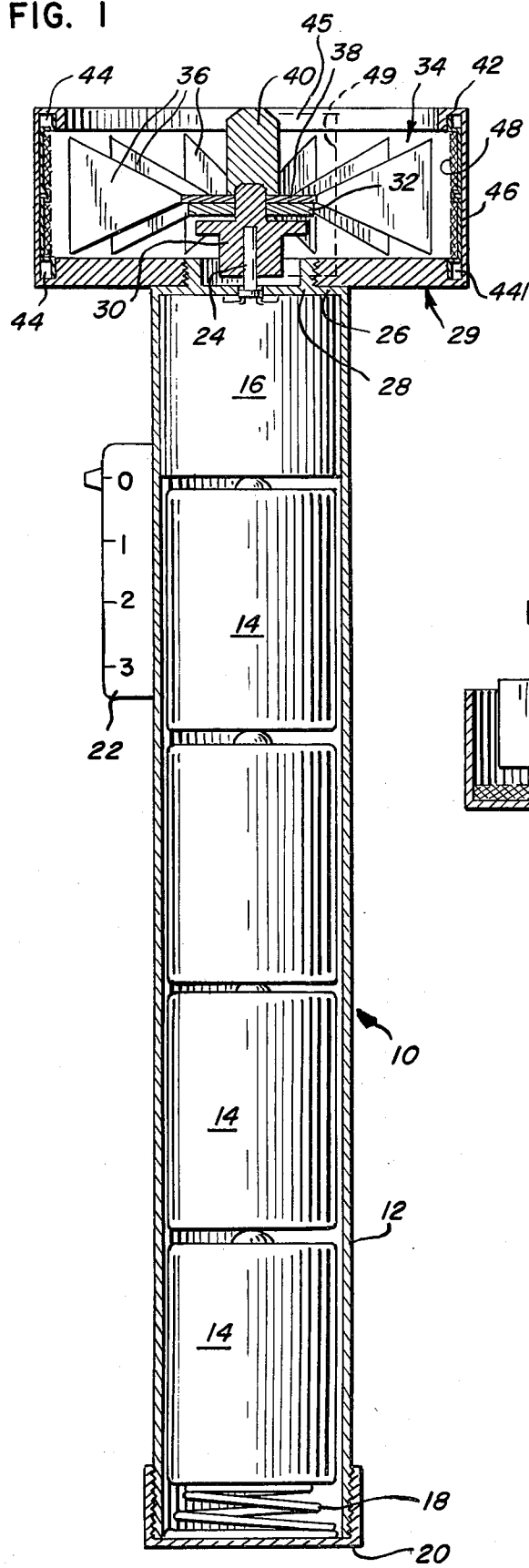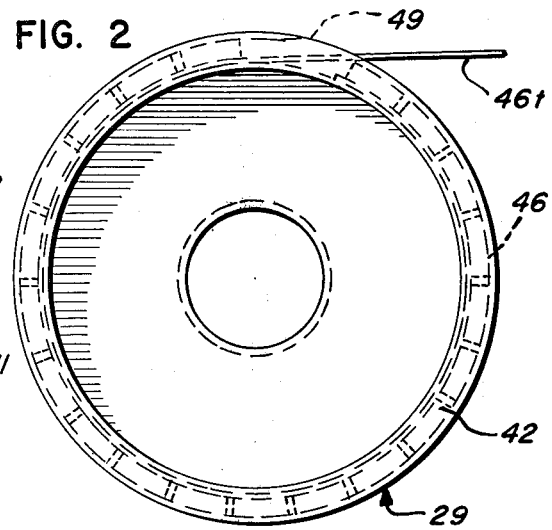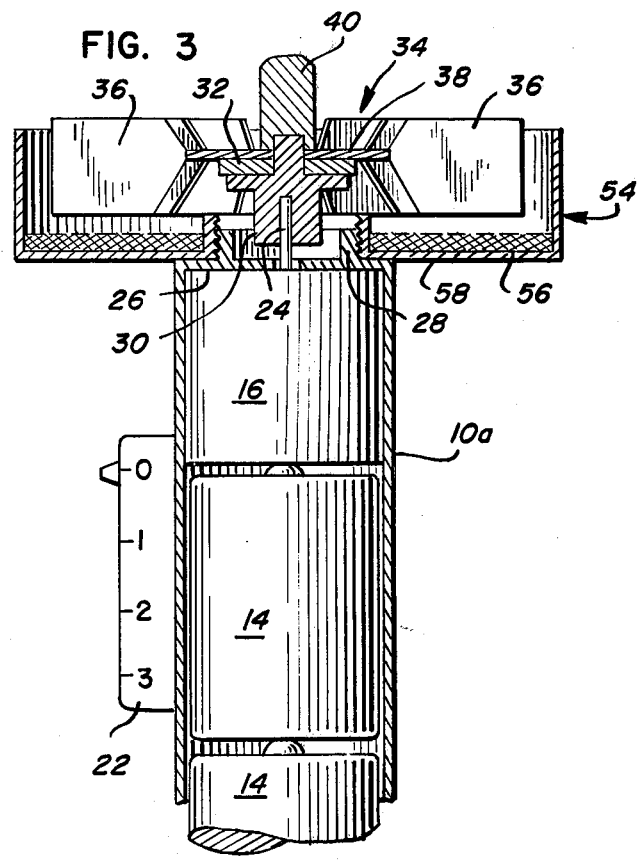

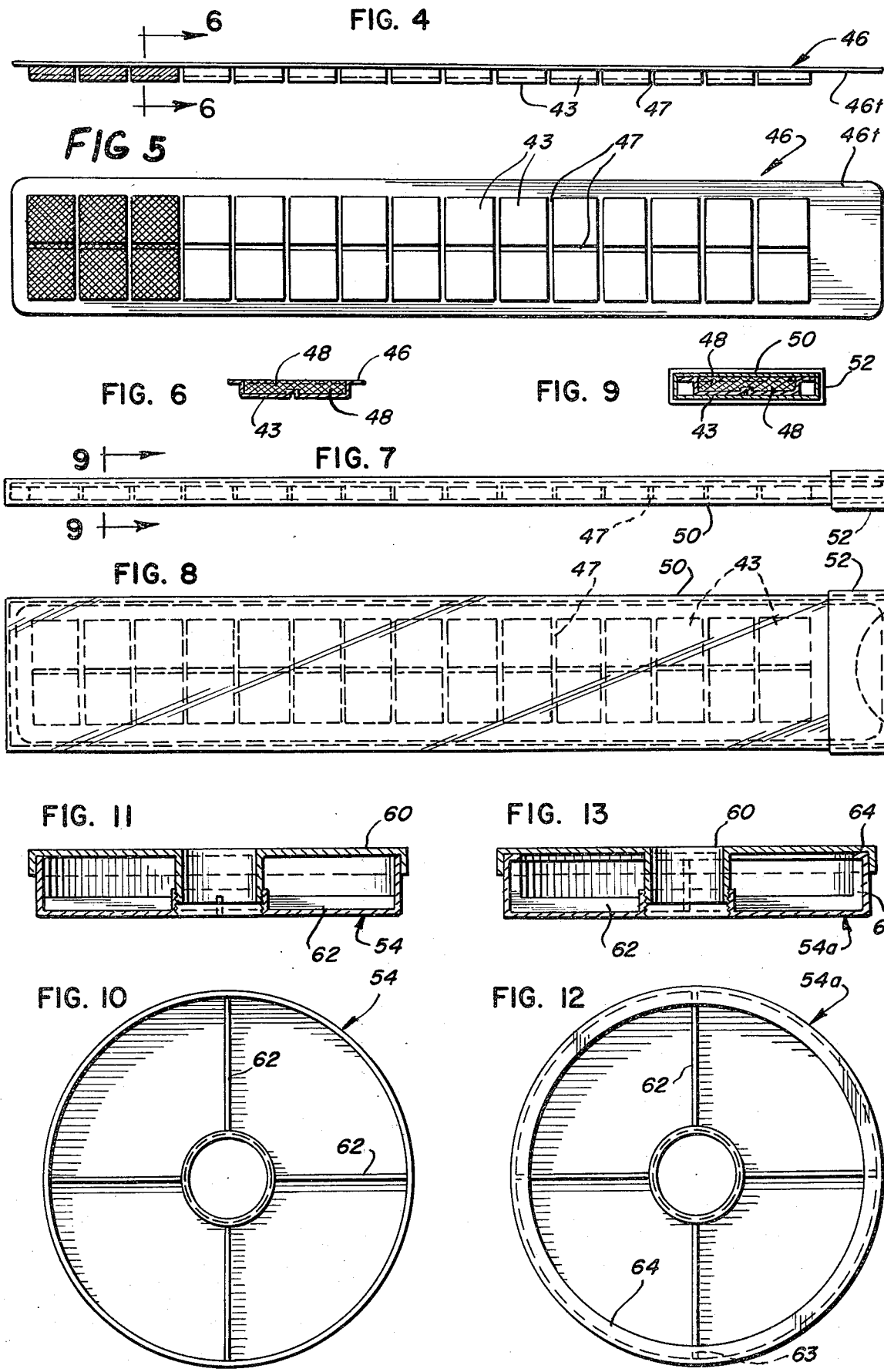

AIR TESTING DEVICE

BACKGROUND OF THE INVENTION

This invention relates to an instrument for testing air or other gaseous bodies, and more particularly pertains to a portable hand-operable testing device for detecting the presence of germs, bacteria and other foreign bodies in large gaseous volumes.

Although the prior art has employed testing devices of the general type hereinafter described, they have heretofore been subject to a serious shortcoming, namely the inability to detect the presence of minute bodies such as germs in large gaseous volumes. The many prior art testing devices which perform quantitative and qualitative analyses of contaminants in the ambient atmosphere have performed with inconsistency. A common assumption employed in testing gaseous volumes, i.e., that germs or other contaminants collected are equally distributed in the atmosphere has been proved to be invalid.

Thus a test of a small portion, e.g. a cubic meter, of a large room for germs will not provide a basis for determining, with any degree of accuracy, the germ content of the entire room. Many prior art testing devices employ small air intake ports which result in the testing of a limited air mass immediately adjacent the intake ports. Conceivably undetected clouds of germs may be in the atmosphere adjacent the limited volume passing through the testing device.

Undetected germs such as those of the Clostridium group can be very dangerous and under certain circumstances fatal. It is thus apparent that testing devices should test large air or other gaseous volumes in the shortest time possible to minimize lack of detection of foreign bodies present.

The necessity for constant atmosphere surveillance is apparent in applications such as the manufacturing and packaging of medicines, pharmaceuticals and the like, food processing plants, in hospitals and other institutions where the aged and/or infirm are present and strict hygienic conditions are to be maintained.

In one embodiment of this invention, the device comprises a battery-operable motor housed in a casing similar to a flashlight casing. Cultural media is disposed in a shallow cup or agar drum attached to one end of the casing, and a motor-driven shaft passes through a central opening in the cup bottom and a plurality of rotatable blades extending from a central hub is mounted on the shaft end. The cup has disposed on its bottom portion surrounding the central aperture and about its inner wall periphery, cultural media adapted to foster the growth of foreign substances whose presence is to be determined. A finger actuatable switch energizes the device motor causing the shaft-driven blades to impel the surrounding atmosphere against the cultural media disposed in the cup. The cultural media is preferably in the form of discrete sections adapted to foster the growth of various specific germs or other foreign substances.

It is thus an object of this invention to provide a hand portable, finger actuatable testing instrument in which a large volume of air or other gas is tested for foreign substances in a short period of time.

It is another object of this invention to provide a testing device which is composed of readily replaceable elements of low cost which may be carried by hand into an area to be tested.

It is a still further object of this invention to provide a testing device which is flexible in operation so as to simultaneously test for a variety of substances in the ambient atmosphere.

The above and other objects of this invention will become apparent from the following detailed description when read in the light of the appended claims and accompanying drawings in which:

FIG. 1 is a longitudinal sectional view of one embodiment of a testing device made pursuant to this invention;

FIG. 2 is a top plan view of a cultural media holding cup employed in the device of FIG. 1;

FIG. 3 is a fragmentary longitudinal sectional view of a testing device made pursuant to this invention employing a modified holding cup;

FIG. 4 is a side elevational view of a flexible cultural media holding strip adapted to be inserted in the cup illustrated in FIGS. 1 and 2;

FIG. 5 is a top plan view of the strip of FIG. 4;

FIG. 6 is a sectional view taken on line 6—6 of FIG. 4;

FIG. 7 is a view similar to FIG. 4 in which the flexible strip is encased in a wrapper;

FIG. 8 is a top plan view of the strip and wrapper of FIG. 7;

FIG. 9 is a sectional view taken on line 9—9 of FIG. 7;

FIG. 10 is a top plan view of a second modified cultural media holding cup adapted to be employed with a testing device of this invention;

FIG. 11 is a sectional view of the cup of FIG. 10 with a cover disposed thereon;

FIG. 12 is a top plan view of a third modified cultural media holding cup adapted to be employed with a testing device of this invention; and FIG. 13 is a sectional view of the cup of FIG. 12 with a cover disposed thereon.

DESCRIPTION OF THE INVENTION

Referring now to FIG. 1, a portable testing device 10 is illustrated having a casing 12 which is preferably of a size to be readily carried in one hand. Disposed in casing 12 are batteries 14 which are urged against the bottom of a battery-energized motor 16 located in the upper end portion of the casing by spring 18 mounted in casing cap 20. Finger-actuatable timer switch 22 mounted on casing 12 regulates the transfer of energizing current from the batteries 14 to motor 16 for predetermined time periods allowed by the various switch settings.

Motor 16 rotatably drives shaft 24 which penetrates casing top 26 and the center of an encompassing threaded stud connector 28, preferably effecting a gas-tight seal at the point of passage. Connector 28 threadably engages the female threads defining the central opening in cultural media cup or drum 29. A flanged coupling 30 is readily engageable with the end of shaft 24 so as to rotate therewith. A magnetic coupling 32 connects coupling 30 with overlying impeller blade assembly 34 having a plurality of blades 36 radially extending from a central hub 38 also mounted on coupling 30. Locking element 40 may be employed to assist in retaining the shaft 24 to the detachable elements mounted thereon. Preferably, though, elements 32, 38 and 40 are rigidly connected to form a single unit that is held by magnetic coupling 32 on the flange of coupling 30 which is permanently secured to shaft 24. Thus this unit is adapted to function as a slip coupling assembly.

It will be most clearly seen from FIG. 1 of the drawing that the drum 29 has an inwardly and downwardly disposed annular lip 42 defining the upper rim thereof. The lip 42 defines a shallow annular channel 44 for reception of the upper edge of a strip such as strip 46 illustrated in FIGS. 4 and 5 which may have sections 48 of cultural media such as agar disposed in open-back pockets 43 formed in the strip (see FIGS. 6 and 9). The media sections 48 are adapted to encourage the growth of specific germs or bacteria whose presence is to be detected in the atmosphere to be tested by the device 10. Regular intervals 47 between the pockets 43 (see FIGS. 4 through 6) facilitate the insertion of the strip 46 in channel 44 by allowing the necessary flexing of the strip. The strip length should be adequate to line the entire inner peripheral wall of the drum 29 and allow a tab portion 46t to remain exteriorly of the drum to allow gripping of the strip without contact with the sections 48. The strip is readily inserted and disposed about the interior of drum 29 by threading through slot 49 with the upper strip edge engaging channel 44 with the lower strip edge engaging opposed channel 44l.

Since the function of the cultural media sections 48 is to detect the presence of foreign substances, they must be kept in a sterile condition until the time of use. This may be effected by wrapper 50 illustrated in FIGS. 7 through 9 which employs a readily removable end section 52. The sections 48 are preferably of different substances adapted to encourage the growth of different foreign bodies.

In the normal course of use, a sterile strip 46 and attached sections 48 are inserted through slot 49 in the apparatus assembly illustrated in FIG. 1 with the open backs of the pockets 43 facing inwardly. The apparatus elements adjacent the strip 46 are sterilized prior to reception of the strip in channel 42, as by contact with a gas or flame to prevent contamination of the cultural media sections 48. Switch 22 is then actuated for the desired time period and motor 16 is energized. Impeller blades 36 impel the adjacent atmosphere entering the open cup and against the peripherally arranged cultural media sections 48 at high speed. The surrounding air or gas is drawn by the rotating blades 36 as the rapid blade rotation creates a low pressure area, drawing air disposed at some distance from the device 10 by virtue of the whirlwind action created by the blades 36.

Intervals 47 between pockets 43 assist in the creation of air turbulence which improves the deposition of the smallest particles on the cultural media sections 48. Also, at the cup rim defined by lip 42, air is drawn into the cup, contacted with the sections 48, discharged and partially drawn back into the cup thereby assuring collection of the particles present in the atmosphere adjacent the device 10.

After the air or other gas has been tested for the desired time period, strip 46 may be readily removed from cup 29 by means of tab portion 46t and reinserted in sterile wrapper 50 for conveying to a breeding chamber to develop the foreign substances which have contacted the sections 48.

For reuse of the device 10 of FIG. 1, the readily detachable components mounted on shaft 24 are sterilized as is the drum 29 prior to insertion of a new strip 46.

FIG. 3 illustrates testing device 10a utilizing a modified cultural media containing cup 54 which does not employ a channel-forming rim portion as does cup 29 of FIGS. 1 and 2. Media 56 is formed on bottom 58 of the cup 54. Prior to use, a gas-tight cover such as cover 60 illustrated in FIG. 11 is retained over the open end of cup 54 to prevent contamination of the cultural media. When ready for use, the cover 60 is removed, the cup screwed onto stud connector 28 and the remaining elements 32, 38 and 40 set in place on the coupling 30 and shaft 24 prior to energizing the device motor 16.

After the desired testing period, the detachable elements 32, 38 and 40 are removed from elements 30 and 24. The cup 54 is disengaged from stud 28 and the cover 60 is again placed on the cup which is removed to the desired breeding chamber. Dividing ridges 62 formed on cup bottom 58 enable a plurality of separated sections of cultural media to be poured or otherwise formed on the cup bottom.

Cup 54a of FIGS. 12 and 13 differs from cup 54 of FIGS. 10 and 11 in that it possesses an inwardly projecting annular flange 64 which facilitates the formation of a wall covering of the cultural media about the inner cup periphery if the covering is cast in the cup. The width of lip 64 may determine the width of the coating formed thereon as by utilizing centrifugal force as the cup is rotated. The strip 46, cups and cup covers, above described, are preferably formed of a transparent plastic material.

It is seen from the foregoing, therefore, that a testing device is provided which may use cultural media in a variety of different forms depending on the specific cup employed with the basic device components. The device may simultaneously test for a plurality of foreign substances and efficiently test large gaseous volumes by means of the partial vacuum created at the vicinity of the cultural media. It is also evident from the foregoing that the device elements are hand portable, simple in nature and inexpensive to manufacture and, yet, efficiently operate in performance of a very important function.

I claim:

1. Hand-held apparatus for testing a body of gaseous fluid for matter suspended therein, said apparatus comprising: casing means wherein said casing means serves as a handle, energy means contained therein; switch means disposed on said casing means and controlling said energy means; rotary drive means within said casing means having a rotary shaft and energized from said energy means through said switch means, said rotary shaft extending from said rotary drive means;

cylindrical container means having its central axis aligned with said rotary shaft and having one container end secured to a surface of said casing adjacent said rotary drive means, the other end being open to said gaseous body;

impelling means disposed on said rotary shaft and driven thereby, wherein said impelling means is disposed within said container means; and substrate means on at least one internal surface of said container means, said impeller means drawing said fluid through said open end and impelling said fluid against said substrate means.

2. The apparatus of claim 1 in which said container means comprises a shallow drum having a central aperture in the bottom thereof, and said rotary shaft passes through said aperture; said substrate means comprising test sheet support means and a test sheet thereon including spaced sections of cultural media secured to a flexible strip disposed about the inner periphery of said drum.

3. The apparatus of claim 1 in which said container means comprises a shallow drum having an aperture in the bottom thereof for passage of said shaft, and said substrate means comprises a shaped bottom surface of said drum and cultural media disposed on said shaped surface and disposed about said aperture.

4. The apparatus of claim 3 in which the shaped surface of the drum bottom is divided into sections by means of ridges; different media segments being disposed in said sections.

5. The apparatus of claim 3 in which said cultural media is also disposed about the inner periphery of said drum.

6. The apparatus of claim 1 in which said impeller means comprises rotatable blades detachably connected to said rotary shaft.

7. The apparatus of claim 1 including a magnetic coupling disposed on the portion of said rotary shaft disposed in said container means; said impeller means being mounted on said coupling so as to be readily detachable from said rotary shaft.

8. The apparatus of claim 1 including a finger-actuatable timer means on said casing means for determining the time during which said rotary drive means is driven by said energy means following actuation of said switch means.

9. Hand-held apparatus for testing a body of gaseous fluid for matter suspended therein, said apparatus comprising:

casing means; energy means contained therein, and rotary drive means within said casing means and energized from said energy means, said rotary drive means driving a rotary output shaft extending beyond a surface of said casing means adjacent to said rotary means;

cylindrical container means having its central axis aligned with said shaft and having one end secured to said surface of said casing means, the other end being open to said gaseous body; means on the inner peripheries of said container ends defining spaced substantially parallel guides; a slot in the cylindrical surface of said container means communicating with said guides whereby a strip may be inserted through said opening into said guides to form a test strip on the internal surface of said cylindrical container means;

and impeller means on said shaft and driven thereby, said impeller means drawing fluid through said open end and centrifugally impelling said fluid against such test strip.

10. The apparatus of claim 9 including, in combination, said test strip which comprises a flexible strip having spaced masses of cultural media secured thereto; said masses encompassing the impeller means, and having regular intervals therebetween whereby turbulence of the impelled gaseous medium within the cylindrical container means is increased.

11. The apparatus of claim 10 in which said strip has a length greater than the circumference of said internal surface so that when said strip is lining the entire circumference of said surface a tab portion of said strip projects outwardly through said opening.

* * * * *